United States Patent [19]

Johnson

[11] Patent Number: 5,549,676

[45] Date of Patent: Aug. 27, 1996

[54] BIOLOGICAL REPLACEMENT LIGAMENT

[76] Inventor: Lanny L. Johnson, 4528 S. Hagadorn Rd., E. Lansing, Mich. 48823

[21] Appl. No.: 307,106

[22] Filed: Sep. 16, 1994

Related U.S. Application Data

[63] Continuation of Ser. No. 120,415, Sep. 14, 1993, abandoned.

[51] Int. Cl.⁶ ........................................................ A61F 2/68
[52] U.S. Cl. ................................................ 623/13; 623/18
[58] Field of Search .................................. 623/11, 12, 13, 623/16, 18, 17, 66

[56] References Cited

U.S. PATENT DOCUMENTS

| | | |
|---|---|---|
| 3,176,316 | 4/1965 | Bodell . |
| 3,797,047 | 3/1974 | Pillet ............................. 623/13 |
| 4,182,339 | 1/1980 | Hardy, Jr. . |
| 4,467,478 | 8/1984 | Jurgutis ......................... 623/13 |
| 4,469,101 | 9/1984 | Coleman et al. . |
| 4,584,722 | 4/1986 | Levy et al. ..................... 623/13 |
| 4,604,097 | 8/1986 | Graves, Jr. et al. . |
| 4,668,233 | 5/1987 | Seedhom et al. . |
| 4,712,553 | 12/1987 | MacGregor ................. 623/13 X |
| 4,792,336 | 12/1988 | Hlavacek et al. . |
| 4,870,966 | 10/1989 | Dellon et al. . |
| 4,942,875 | 7/1990 | Hlavacek et al. . |
| 5,004,474 | 4/1991 | Fronk et al . |
| 5,015,253 | 5/1991 | MacGregor . |
| 5,059,211 | 10/1991 | Stack et al. . |
| 5,078,744 | 1/1992 | Chvapil . |
| 5,116,337 | 5/1992 | Johnson . |
| 5,116,372 | 5/1992 | Laboureau . |
| 5,141,522 | 8/1992 | Landi . |
| 5,147,399 | 9/1992 | Delon et al. . |
| 5,147,400 | 9/1992 | Kaplan et al. ............................. 623/13 |
| 5,152,763 | 10/1992 | Johnson . |
| 5,171,274 | 12/1992 | Fluckiger et al. . |
| 5,176,708 | 1/1993 | Frey et al. ................................. 623/13 |
| 5,192,322 | 3/1993 | Koch et al. . |
| 5,197,983 | 3/1993 | Berman et al. . |
| 5,217,495 | 6/1993 | Kaplan et al. ............................. 623/13 |

FOREIGN PATENT DOCUMENTS

| | | | |
|---|---|---|---|
| 0498690 | 8/1992 | European Pat. Off. ................. 623/13 |
| 0561710 | 9/1993 | European Pat. Off. . |

*Primary Examiner*—David Isabella
*Attorney, Agent, or Firm*—Cushman Darby & Cushman

[57] ABSTRACT

A biological replacement ligament is provided which includes a compressible core and a separate flexible outer sheath having a first end, a second end, and a generally tubular intermediate portion. The intermediate portion surrounds the compressible core, whereby the application of tension between the first and second ends causes the intermediate portion to constrict upon the compressible core thereby allowing elongation of the ligament to modulate the tension between the first and second ends. The amount of elongation and tension modulation is primarily determined by the compressibility of the core.

14 Claims, 5 Drawing Sheets

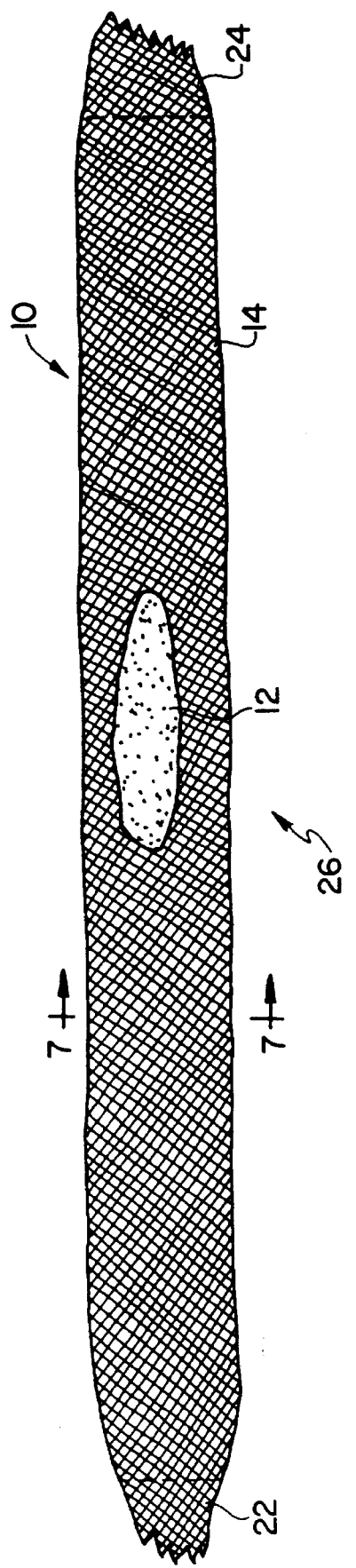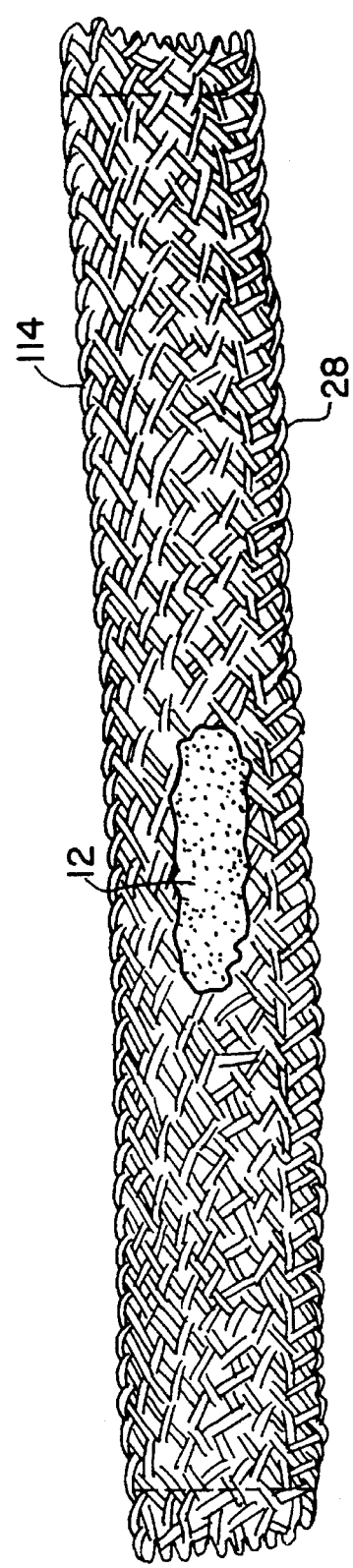
FIG. 1
FIG. 2

BIOLOGICAL REPLACEMENT LIGAMENT

This is a continuation of application Ser. No. 08/120,415, filed on Sep. 14, 1993, which was abandoned upon the filing hereof.

BACKGROUND OF THE INVENTION

1. Field of the Invention

This invention relates to prosthetic devices for connecting tissue, more particularly to a biological replacement ligament which reproduces the function of a natural collateral or cruciate ligament.

2. Background Information

Conventionally, damaged anterior cruciate ligaments are replaced with grafts from other patient tissue, such as tendon tissue. However, in certain circumstances, the fixation of the replacement ligament is not adequate, requiring further surgery. Prosthetic devices have been used in place of natural connecting tissue, but these devices also exhibit unsatisfactory fixation. Further, the prosthetic devices do not function as would the natural anterior cruciate ligament.

U.S. Pat. No. 5,147,400 discloses a ligament prosthesis which is intended to approximate the biomechanical characteristics of the natural tissue to be replaced or augmented. U.S. Pat. No. 5,147,400 provides a prothesis having a core composed of a first yarn and a sheath surrounding the core and fabricated by a second yarn. However, when significant tension is applied between the ends of the prothesis, interstitial tearing of yarns may occur, much like tearing of individual fibers of a rope under tension. Further, excessive creep elongation may occur as a result of the extreme forces placed on the ligament. Thus, under extreme stress, the prosthesis may be damaged, and therefore may not exhibit the function of the natural ligament.

As is apparent from the foregoing, state of the art ligament prostheses fail to produce predictable and satisfactory results of reproducing the function of the natural ligament.

SUMMARY OF THE INVENTION

It is an object of the invention to provide a biological replacement ligament which reproduces the function of a natural ligament, particularly anterior and posterior cruciate ligaments. It is a further object of the invention to provide a biological replacement ligament which will allow reconstitution of the repaired structure permitting ingrowth of fibrous tissue.

In accordance with the principles of the present invention, this objective is obtained by providing a biological replacement ligament which includes a compressible core and a separate, flexible outer sheath having a first end, a second end, and a generally tubular intermediate portion. The intermediate portion surrounds the compressible core, whereby the application of tension between the first and second ends causes the intermediate portion to constrict upon the compressible core thereby allowing elongation of the ligament, to modulate the tension between the first and second ends. The amount of elongation and tension modulation is primarily determined by the compressibility of the core.

Other objects, features and characteristics of the present invention, as well as the methods of operation and functions of the related elements of the structure, and the combination of parts and economies of manufacture, will become more apparent upon consideration of the following detailed description, and the appended claims with reference to the accompanying drawings, all of which form a part of this specification.

BRIEF DESCRIPTION OF THE DRAWINGS

FIG. 1 is perspective view of a biological replacement ligament having a mesh-like outer sheath shown partially removed for clarity of illustration, provided in accordance with the principles of the present invention;

FIG. 2 is a perspective view of the biological replacement ligament of FIG. 1 having a braided outer sheath;

DETAILED DESCRIPTION OF THE PRESENTLY PREFERRED EXEMPLARY EMBODIMENTS

Figure 4:
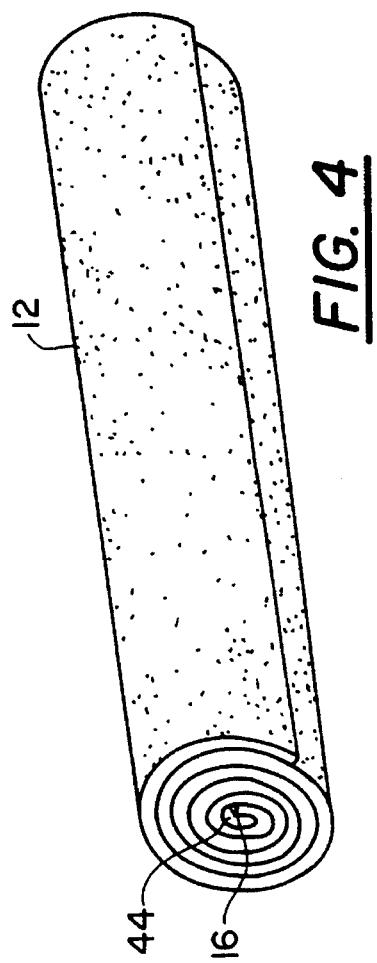
FIG. 4 is a perspective view of a core member of the biological replacement ligament provided in accordance with the principles of the present invention.
Figure 6:
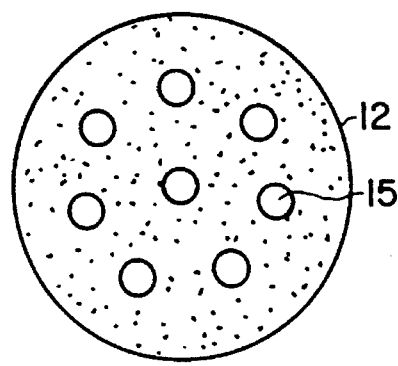
FIG. 6 is an end view of yet another embodiment of the core member provided in accordance with the principles of the present invention.
Figure 7:
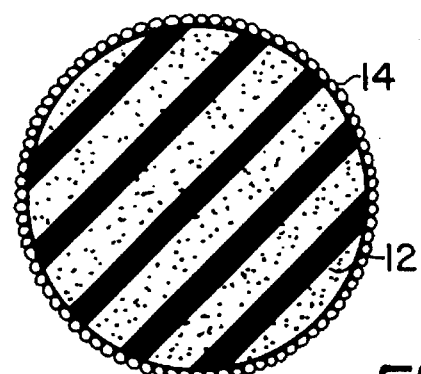
FIG. 7 is an enlarged sectional view taken along the line 7—7 in FIG. 1.

Referring to the drawings, a biological replacement ligament is generally indicated at 10. The replacement ligament 10 includes a cylindrical core member 12 surrounded by an outer sheath 14. The core member 12 is preferably made of compressible and resilient material such as a foamed, rubber-like material FIG. 7. It can be appreciated that the core member may be composed, for example, of open or closed cell foamed rubber, natural material, synthetic materials such as rubber, silicone and plastic, ground and compacted material, perforated material, and/or a compressible solid material. The core member may be made of permanent, and/or of biodegradable materials such as polymers and copolymers of plastics, lactic acid and/or glycalic acid. The core member may be a solid cylindrical member, cylindrical member having hollow cavities 15 (FIG. 6), a tube, or a flat sheet rolled into a tube so as to define a hollow cavity 16 (FIG. 4).

Figure 5:
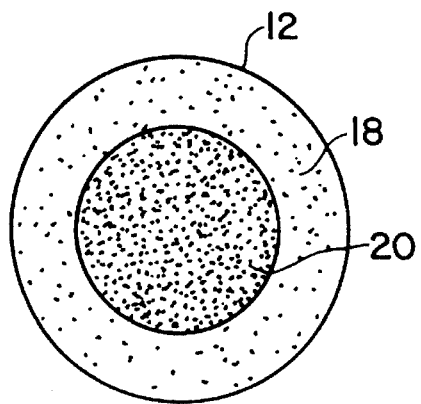
FIG. 5 is an end view of another core member provided in accordance with the principles of the present invention.

As shown in FIG. 5, the core member 12 may include first portion 18 and a second portion 20, each having different degrees of compressibility for modulating stresses applied to the replacement ligament, as will become apparent below.

Figure 3:
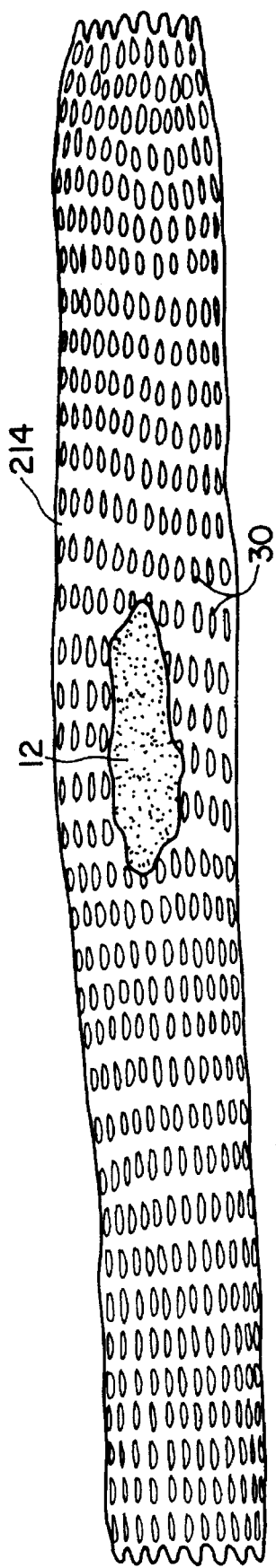
FIG. 3 is a perspective view of the biological replacement ligament of FIG. 1 having a perforated outer sheath.

The outer sheath 14 may be formed in a variety of configurations, examples of which are shown in FIGS. 1–3. Thus, as illustrated in FIG. 1, the outer sheath 14 is a flexible, finely-woven sheath mesh of synthetic material defining a plurality of spaces therein. The outer sheath 14 may be biodegradable, for example, composed of a polylactide material or may be non-biodegradable. The outer sheath 14 includes a first end 22 and a second end 24. Both ends extend beyond ends of the core member for attachment to bone or other tissue. The ends may define tubular portions for receiving a clamping plug to attach the replacement ligament to bone, as will become more apparent below. An intermediate, generally tubular portion 26 is defined between ends 22 and If both the core member and the outer sheath are made of permanent or non-biodegradable materials, it can be appreciated that they can be replaced with time, wear or re-tear.

FIG. 2 shows a biological replacement ligament that is identical to that of FIG. 1, except that the outer sheath 114 is made of a flexible interwoven braid 28. The braid is tightly woven and differs from the sheath mesh in that no are evident. The junctures of filaments of the interwoven braid may be joined together, or be movable with respect to each other.

FIG. 3 shows a further variation of the biological replacement ligament which is identical to that of FIG. 1, except that the outer sheath 214 is a film having a plurality of perforations 30 therein.

The biological replacement ligament 10 may be attached to bone in a variety of ways. FIGS. 8–12 illustrate preferred attachments of the replacement ligament to bone. Although the ligament must be attached to the two bones to be joined thereby, only one end of the replacement ligament 10 attached to bone 32 is shown with the outer sheath being partially cut away to show how it surrounds the core member 12. It can be appreciated that the other end of the ligament is similarly attached to the other bone to be joined by the replacement ligament.

Figure 8:
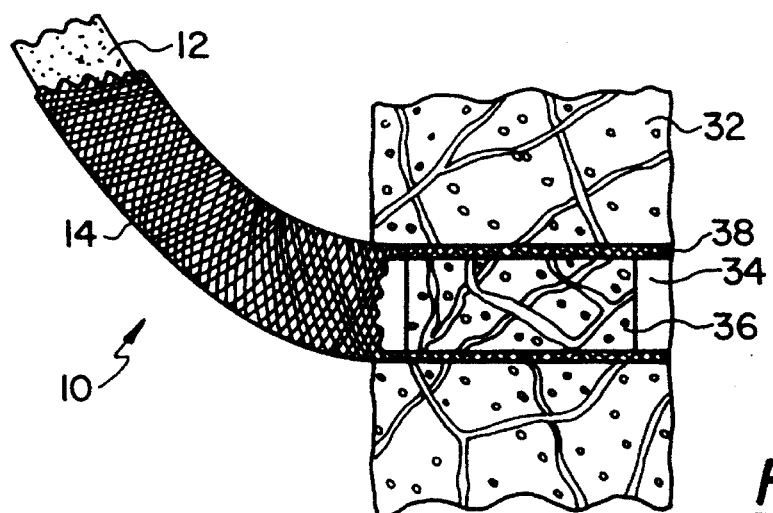
FIGS. 8–12 are schematic representations showing one end of the biological replacement ligament attached to bone.

Referring to FIG. 8, a bore 34 is provided in a bone 32 at the region where the original ligament was attached. The bore 34 is formed by removing a cylindrical plug of bone. One end of the replacement ligament 10 is inserted into the bore 34. Next, a bone plug 36 or another plug of permanent or bioabsorbable material is inserted into the open tubular end 38 of the outer sheath and is moved therealong into the bore to secure the ligament between the plug and the bone 32. Other fixation devices may be employed such as the use of fasteners or the use of a wedge member. The perforations, braids or mesh-like openings in the outer sheath promote bone growth through the synthetic fabric to ensure reliable fixation of the replacement ligament to the bone over time.

Figure 9:
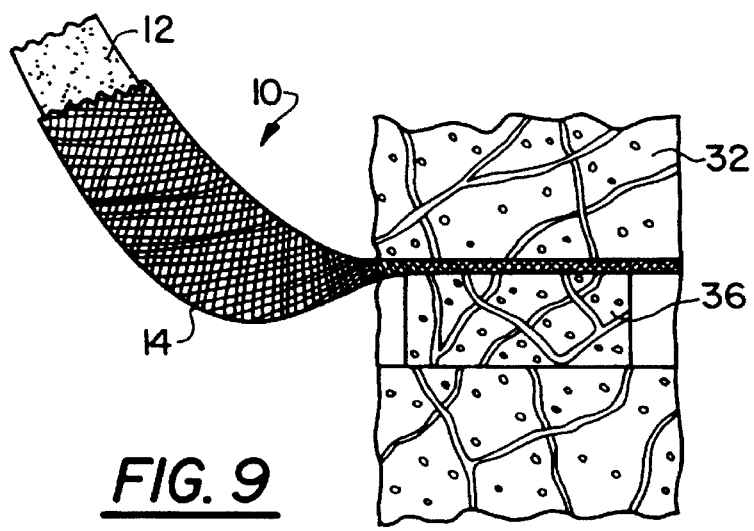

FIG. 9 shows another example of attaching the replacement ligament 10 to the bone. As shown, instead of inserting the bone plug 36 into the tubular end of the outer sheath, the outer sheath is secured by the bone plug 36 wedging the end of the sheath against the wall of the bore 34. Again, bone growth is promoted to further enhance fixation of the replacement ligament to bone.

Figure 10:
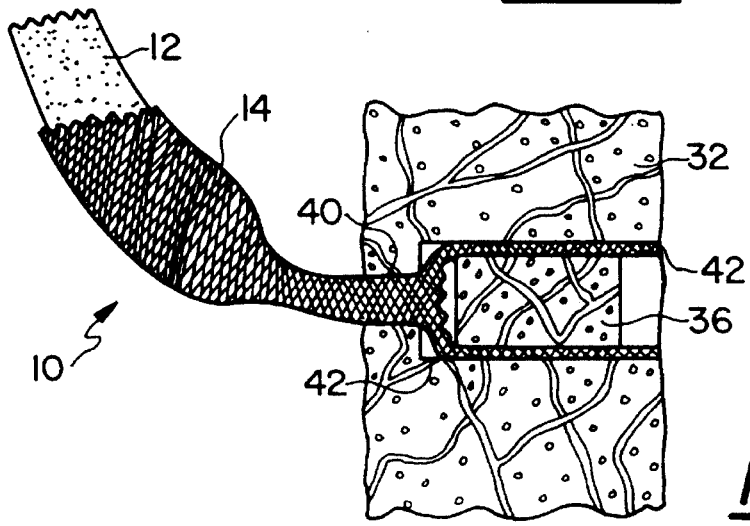

FIG. 10 shows a variation of the attachment of the replacement ligament shown in FIGS. 8 and 9. As shown, the bone 32 includes a reduced diameter portion 40 and an enlarged diameter portion 42. The end of the outer sheath is threaded through the reduced diameter portion and the bone plug 36 is inserted into the tubular end thereof to secure the ligament to the bone 32. The increased diameter portion provides a larger surface for attachment while the reduced diameter portion provides a more localized attachment point.

Figure 11:
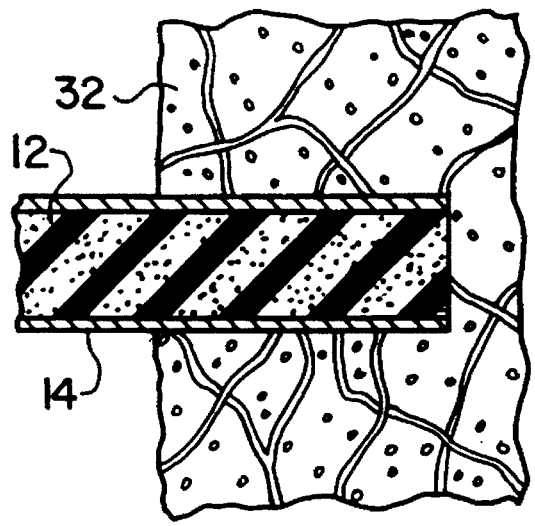

FIG. 11 shows yet another example of attaching the replacement ligament 10 to bone. As shown, both the core member 12 and outer mesh 14 are affixed to the bone 32.

Figure 12:
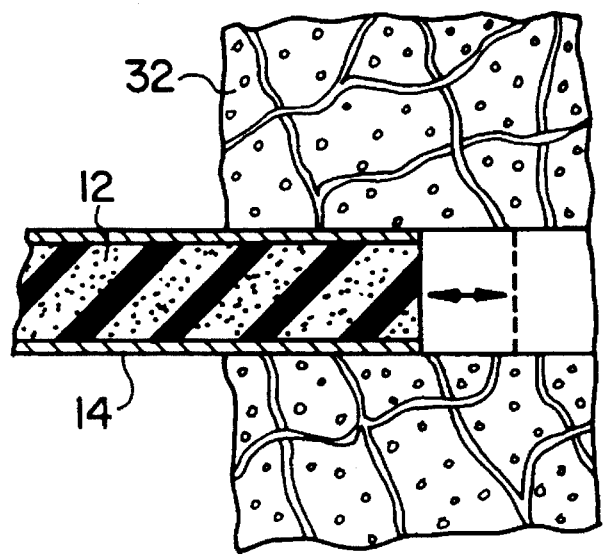

FIG. 12 shows still another way to connect the ligament 10 to bone 32. As shown, the ligament is disposed in a free-floating manner within a bore or socket in bone 32 at one or both ends thereof at an optimal point, determined by normal patient motions. Thus, the free-floating of the ligament provides an optimal tension and fixation during patient motion.

The biological replacement ligament may also be attached to remaining portions of the natural ligament, for example, by sutures.

The function of the biological replacement ligament 10 will be described with reference to FIG. 1. Each end of the replacement ligament 10 is attached to a respective one of the two bones to be joined by the ligament, for example, by one of the aforementioned methods. When stress is applied longitudinally to the outer sheath, the outer sheath constricts, much like a "finger trap", against the core member which results in modulation of the strain. Force due to the tension between the ends of the replacement ligament is initially absorbed in the outer sheath, transferred to the compressible core and subsequently transferred to bony attachments and dampened. This advantageously reduces the force on the ligament fixation point at each end, reproducing the function of a natural ligament.

At present, cruciate ligament grafting in the knee is performed with a patient's own tendon tissue. Studies of these grafts show that the reconstituted ligament is composed of two distinct tissues, the graft and the surrounding fibrous tissue. It is the surrounding fibrous tissue that takes-up the initial slack to stabilize the knee. The original graft affords some subsequent restraint at extremes of stress.

It is preferable that the biological replacement ligament 10 have the biological capacity to form fibrous tissue in, or around it whereby the biological ligament is slowly absorbed as the fibrous tissue replacement occurs. Certain materials, such as talcum powder and crystalline material may be provided with the ligament to invoke a fibrous tissue reaction.

Further, to facilitate fibrous tissue formation and/or stimulate healing natural biological products may be placed in or on the core member 12. For instance, a biological product 44 may be placed in the interior of the roll 16 of the core FIG. 4 or the cavities 15 of core (FIG. 5). The natural products may include blood, marrow, ligament fragments, tendon, growth factors and/or cartilage and/or bone. Further, the stimulus for the fibrosis could be inherent in the biological material of the core member, or another material combined with the primary material of the core member.

It can be appreciated that the replacement ligament of the invention provides a compressible core member that results in modulation of forces exerted thereto, to protect the ligament from either pulling out of the bone or rupturing. The "finger trap" compresses the core member which reduces both the amplitude and length of the terminal force.

Although the present invention has been described with reference to cruciate ligament substitution or reconstruction, it can be appreciated that the invention may have uses in collateral ligaments, medial and lateral, and/or substitution for tendons instead of grafts. Further, in flat form, the invention could be used for hernial defects instead of fascia, Gortex™, Mortex™ or wire mesh, as is conventionally employed.

While the invention has been described in connection with what is presently considered to be the most practical and preferred embodiment, it is understood that the invention is not limited to the disclosed embodiment, but, on the contrary, is intended to cover various modifications and equivalent arrangements included within the spirit and scope of the appended claims.

What is claimed is:

1. A biological replacement ligament sized and shaped to simulate a natural ligament, comprising:

a compressible core of resilient material formed as a unitary mass; and a separate, flexible outer sheath having a first end, a second end, and a generally tubular intermediate portion, the intermediate portion surrounding the compressible core with the first and second ends extending beyond respective opposite ends of the compressible core, the outer sheath being constructed and arranged with respect to the compressible core such that the application of tension to the first and second ends causes the intermediate portion to constrict upon the compressible core thereby allowing elongation of the ligament and modulation of the tension on the first and second ends.

2. A biological replacement ligament sized and shaped to simulate a natural ligament, comprising:

a compressible core formed from a foamed material; and a separate, flexible outer sheath having a first end, a second end, and a generally tubular intermediate portion, the intermediate portion surrounding the compressible core, whereby the application of tension to the first and second ends causes the intermediate portion to constrict upon the compressible core thereby allowing elongation of the ligament and modulation of the tension between the first and second ends.

3. A biological replacement ligament as in claim 1, wherein the compressible core comprises a flat sheet rolled into a tube.

4. A biological replacement ligament as in claim 1, 2 or 3, wherein the core is formed with at least one hollow cavity.

5. A biological replacement ligament as in claim 4, further comprising:

a fibrosis stimulus disposed in the hollow cavity of the core.

6. A biological replacement ligament as in claim 1 or 2, wherein the intermediate portion is constructed of an interwoven braid.

7. A biological ligament as in claim 6, wherein the interwoven braid is formed by filaments braided with crossover junctures.

8. A biological replacement ligament as in claim 6, wherein crossover junctures of the interwoven braid are movable with respect to each other.

9. A biological replacement ligament as in claim 1 or 2, wherein the intermediate portion is a mesh.

10. A biological replacement ligament as in claim 1 or 2, wherein the intermediate portion is constructed of perforated film.

11. A biological replacement ligament as in claim 1 or 2, wherein the core comprises a first portion having a degree of compressibility and a second portion having a different degree of compressibility.

12. A biological replacement ligament as in claim 1 or 2, wherein a portion of one of the first and second ends is tubular for receiving a clamping plug.

13. A biological replacement ligament as in claim 1 or 2, wherein the ligament is constructed of biodegradable materials.

14. A biological replacement ligament as in claim 1, wherein the compressible core is constructed from a solid material.

* * * * *